United States Patent [19]

Frigg

[11] Patent Number: 5,002,542
[45] Date of Patent: Mar. 26, 1991

[54] PEDICLE SCREW CLAMP
[75] Inventor: Robert Frigg, Wayne, Pa.
[73] Assignee: Synthes U.S.A., Paoli, Pa.
[21] Appl. No.: 428,907
[22] Filed: Oct. 30, 1989
[51] Int. Cl.⁵ .............................................. A61F 5/04
[52] U.S. Cl. ........................................ 606/61; 606/72
[58] Field of Search ....................... 606/54, 57, 59, 60, 606/61

[56] References Cited
U.S. PATENT DOCUMENTS

| | | | |
|---|---|---|---|
| 752,828 | 2/1904 | Devine | 403/256 |
| 2,250,417 | 7/1941 | Ettinger | 606/59 |
| 2,346,346 | 4/1944 | Anderson | 606/56 |
| 4,135,505 | 1/1979 | Day | 606/73 |
| 4,349,017 | 9/1982 | Sayegh | 606/59 |
| 4,456,004 | 6/1984 | Kenny | 606/59 |
| 4,483,334 | 11/1984 | Murray | 606/59 |

FOREIGN PATENT DOCUMENTS 0242708 10/1987 European Pat. Off. ...... 128/92 YM

Primary Examiner—Robert A. Hafer
Assistant Examiner—Charles H. Sam
Attorney, Agent, or Firm—Davis Hoxie Faithfull & Hapgood

[57] ABSTRACT

A pedicle screw clamp comprising two sections adapted to form a socket which receives the head of a pedicle screw, a hook which holds a spinal support rod at an adjustable distance from the socket and compression means which holds the two sections together so that they tightly clamp the head of the pedicle screw.

29 Claims, 2 Drawing Sheets

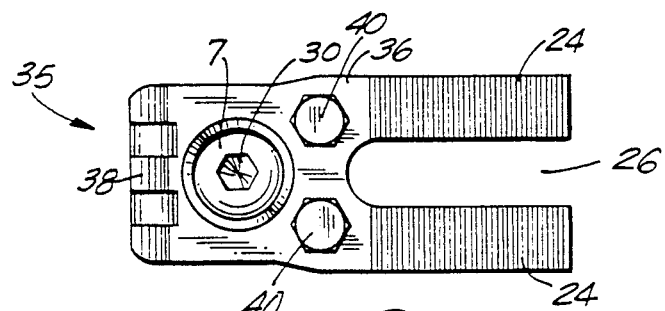
FIG. 5
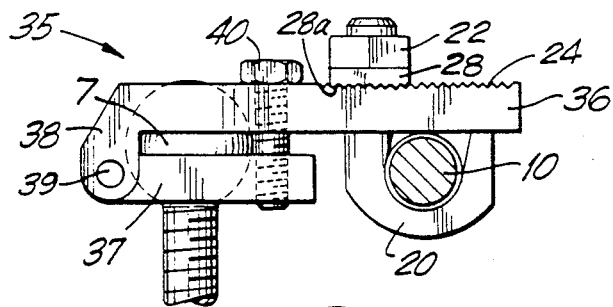
FIG. 4
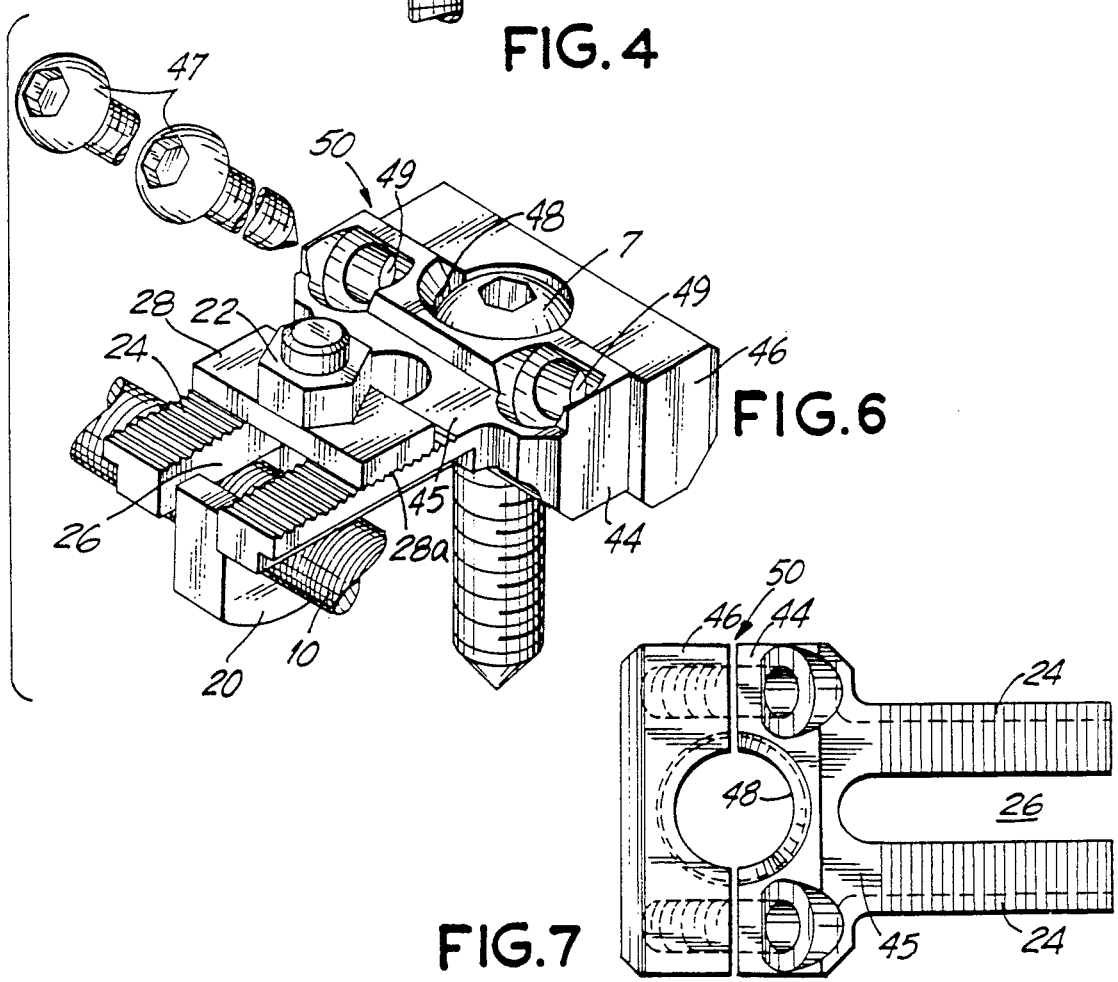
FIG. 6
FIG. 7

PEDICLE SCREW CLAMP

FIELD OF THE INVENTION

The invention relates to a clamp for holding a pedicle screw to a rod used for straightening the spine.

BACKGROUND OF THE INVENTION

Pedicle screws are one type of implant used for treating spinal injuries and deformities. In one common treatment, pedicle screws are driven into the pedicles of vertebrae above and below the injured vertebra or vertebrae. A rod is attached to the pedicle screws, for example, by clamps or by threading it through slots in the screws. The rod holds the spinal column approximately in its desired alignment, thereby relieving pressure on the injured vertebra or vertebrae and permitting it to heal and regain its natural conformation. One type of pedicle screw is disclosed in U.S. patent application Ser. No. 163,278, filed Mar. 2, 1988, commonly assigned herewith.

As noted, clamps may be used to connect rigidly the part of the pedicle screw protruding from the vertebra to a spinal support rod. Most of the pedicle screw clamps currently known maintain a fixed distance between the pedicle screw and the support rod and many do not permit relative angular adjustment of the screw and support rod. Thus, current clamps do not allow sufficient adjustment to the specific alignment required by each patient's needs.

SUMMARY OF THE INVENTION

In accordance with the invention there is provided a clamp for a pedicle screw which will enable the screw to be attached to a support rod with an adjustable distance between the axis of the screw and the axis of the rod, and at the same time permitting angular adjustment of the axis of the screw relative to the axis of the rod. The clamp may comprise two sections adapted to receive the head of a pedicle screw, a hook which holds the support rod at an adjustable distance from the pedicle screw and compression means which holds the two sections together so that they tightly clamp the head of the pedicle screw.

In one aspect the invention comprises a clamp having a jaw with upper and lower sections, hinged at one end, said sections being bifurcated to form a slot extending through the sections, a socket formed in the jaw for receiving the head of a pedicle screw and compression means movable relative to said socket for forcing the jaws together, said compression means being adapted to receive a support rod and being operable to urge said rod against the jaw as the jaw sections are forced together.

In another aspect the invention comprises a clamp having a jaw with an upper section and a shorter lower section, hinged at one end, said upper section being bifurcated to form a slot extending through it, a socket formed in the jaw for receiving the head of a pedicle screw, receiving means which receives a support rod and holds the rod against the lower surface of the upper section, and compression means, such as a screw extending through the upper and lower sections, which forces them together so as to grasp the head of the pedicle screw.

In another aspect the invention comprises a clamp having front and back sections which form a socket for the pedicle screw head, the front section having a bifurcated extension. The clamp further comprises receiving means which receives a support rod and holds it against the lower surface of the extension and compression means, such as a screw which holds the front and back sections together, grasping the head of the pedicle screw.

In another aspect the invention includes a fixation assembly comprising a clamp as described, a pedicle screw having a head shaped to engage the socket and a support rod.

DESCRIPTION OF THE DRAWINGS

The invention will be further disclosed with reference to the accompanying drawings, wherein:

FIG. 4 is a side view of another embodiment of a fixation assembly according to the invention;

FIG. 5 is a plan view of the clamp and pedicle screw of FIG. 4;

FIG. 6 is a perspective view of another embodiment of a fixation assembly according to the invention; and FIG. 7 is a top view of the clamp of FIG. 6.

DETAILED DESCRIPTION OF THE INVENTION

Figure 1:
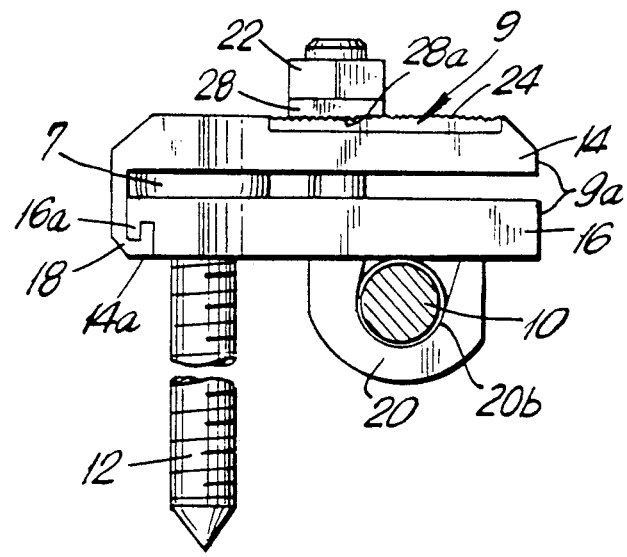
FIG. 1 is a side elevational view of a fixation assembly according to the invention showing the support rod in crosssection.

As shown in FIG. 1, a clamp 9 according to the invention holds a support rod 10 (which may be threaded) and a pedicle screw 12 in a fixed position, more or less perpendicular to each other. The clamp 9 comprises a jaw 9a having an upper section 14 and a lower section 16, connected to each other by a C-shaped extension 14a of upper section 14 which engages a flange 16a of lower section 16 to form a hinge 18. Towards their ends near hinge 18, upper and lower sections 14 and 16 are shaped to form a socket 8 (FIG. 3) adapted to accommodate the head 7 of a pedicle screw 12. In a preferred embodiment of the assembly of the invention, the pedicle screw has an essentially spherical head. The upper section 14 of jaw 9a has an aperture 14b providing access to the screw head 7. Lower section 16 has an aperture 16b to accommodate the shaft of the pedicle screw 12.

The surface of the head of pedicle screw 12 may be roughened to provide better grip by the clamp. The inner surfaces of the socket 8 which holds the head may also be roughened.

Figure 2:
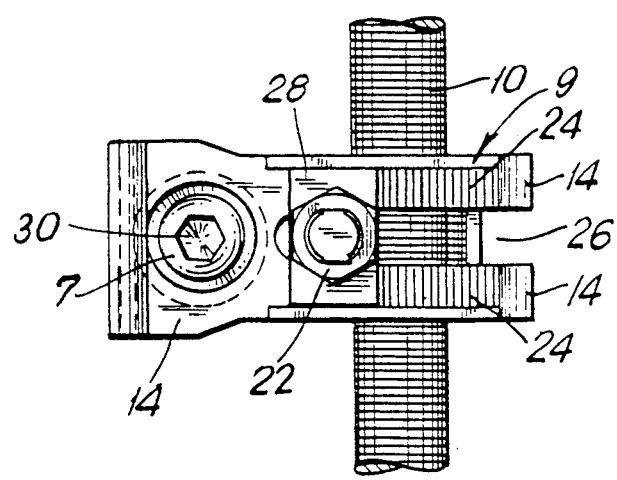
FIG. 2 is a plan view of the assembly of FIG. 1.
Figure 3:
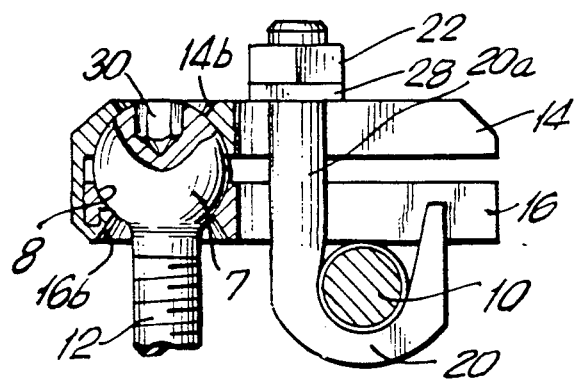
FIG. 3 is a side view of the assembly of FIGS. 1 and 2, partially cut away to show the entire head of the pedicle screw.

Compression means are provided to press the upper and lower sections 14 and 16 of the jaw 9a together. As shown in FIGS. 1-3 the compression means may be a hook 20. As shown in FIGS. 2 and 3, the upper and lower sections 14 and 16 are bifurcated to provide a through slot 26. The shaft 20a of hook 20 passes through this slot. The bight 20b of hook 20 forms a space under lower section 16 adapted to receive a support rod 10. The inner surface of bight 20b may be threaded or otherwise roughened to engage threads or a roughened surface on support rod 10. The lower surface of lower section 16 may be threaded, knurled or otherwise roughened in the area where it contacts support rod 10, in order to engage threads or the like on the support rod. The textured surfaces provide for a better grip on the support rod, which must be held firmly in place.

The upper surface of upper section 14 has toothed areas 24 along the sides of slot 26. A small retaining plate 28 with teeth 28a on one surface rests on top of and bridges the toothed areas 24, with the two sets of teeth interlocking. The distance between the shaft 20a of hook 20 and the pedicle screw can be varied by moving the small toothed plate 28 along the length of slot 26. Nut 22 is threaded on the hook shaft on top of plate 28. Tightening nut 22 locks plate 28 and hook 20 into the desired place along slot 26.

In using the device according to the invention, the pedicle screw is first run through the aperture 16b in the lower jaw section 16 and inserted into the bone, using the hexagonal socket 30 in the head of the screw to receive a suitable tool. The upper section 14 is then engaged with lower section 16 to form a jaw. Hook 20 is loosely inserted in slot 26 and the support rod 10 inserted in the bight of the hook, the hook being moved along the slot to the desired position. When screw 12 and rod 10 are at the optimum distance from one another and at the proper angle, nut 22 is turned down on the shaft of the hook, forcing the jaw sections together to clamp the head of the screw in its socket and press rod 10 firmly against lower section 16. The leverage provided by the jaw construction enables the screw to be tightly fixed in its selected position relation to the support rod.

Another embodiment of the invention is shown in FIGS. 4 and 5. Clamp 35 comprises a bifurcated upper section 36 and a lower section 37, connected to each other by a hinge 38 with a pin 39. On the side of pedicle screw 12 opposite the hinge 38 are two threaded screws 40. These screws hold upper section 36 and lower section 37 together, thus locking the head 7 of pedicle screw 12 in place. FIG. 5 shows two screws 40, but in an alternative embodiment, a single screw may be used.

Lower section 37 is shorter than upper section 36, as shown in FIG. 4. A hook as described in connection with FIGS. 1-3 passes through the slot 26 formed by the bifurcation of upper section 36 and holds a support rod against the lower surface of upper section 36. It should be evident that the configuration of the toothed upper surface, small retaining plate and nut described in connection with FIGS. 1-3 are applicable to this embodiment as well.

The manner of use of the embodiment of FIGS. 4 and 5 is parallel to that of FIGS. 1-3.

Another embodiment of the invention is shown in FIGS. 6 and 7. In this embodiment the head of the pedicle screw instead of being clamped by two hinged elements is held between two sections of a block which are joined by screws or bolts.

Referring to FIG. 6, the clamp in this embodiment comprises a block 50 having a front section 44 and a back section 46. Front section 44 has a bifurcated extension 45 which forms a slot 26. As shown in FIG. 6 a hook 20, support rod 10, toothed upper surface 24, small toothed plate 28 and nut 22 are provided as described above in connection with FIGS. 1-5. Front section 44 has two screw holes 49 through it. As shown in FIG. 6, these holes are at an angle of about 45° to the top surface of the clamp or the axis of the pedicle screw 12 to be retained in the clamp. These screw holes 49 continue into back section 46 at the same angle. In a preferred embodiment, only the parts of screw holes 49 which are in the back section 46 are threaded, while screws 47 may be partially or wholly threaded.

Front and back sections 44 and 46 are shaped to form a socket 48 which accommodates the head 7 of a pedicle screw 12. Engagement of screws 47 into the threaded holes in back section 46 forces the back section 46 against front section 44 and secures pedicle screw 12 in its desired position.

When using this embodiment of the invention, the pedicle screw is inserted into the bone. Front section 44 is placed on the front of the screw head, with a hook inserted in slot 26 and the support rod held in the bight of the hook. When the pedicle screw and rod are adjusted to the optimum distance and angle, back section 46 is placed on the back of the pedicle screw head. Screws 47 are inserted into screw holes 49 and tightened. In the embodiment shown in FIG. 6, screws 47 have hexagonal holes in their heads to receive a tool for tightening them.

The 45° degree angles make it easier for the surgeon to reach the screws 47. In an alternative configuration (not shown) the screws are put in straight from back section 46 to front section 44, with the axis of the screw holes parallel to the extension 45 or generally perpendicular to the axis of the pedicle screw.

The ends of extension 45 may be flanged as shown in FIG. 6, or they may have a simple rectangular cross-section, on any of the embodiments of the invention.

The various surfaces described in connection with FIGS. 1-3, as being roughened to provide better grip may of course be employed in the other embodiments.

From a consideration of the foregoing description it will be evident that a clamp according to the invention permits movement of the support rod relative to the pedicle screw. The surgeon can therefore regulate the horizontal distance between the pedicle screw and the support rod. Because the spherical head of the screw may be tilted in its socket the angle between the screw and the support rod may also be adjusted. Thus the clamp permits the surgeon to adjust each pedicle screw to the specific configuration required by a particular patient.

Although the invention has been described as applied to a pedicle screw, it is clearly also applicable to other similar devices such as spinal hooks.

What I claim is:

1. A clamp for attaching a spinal implant to a spinal support rod comprising:
    a first section and a second section, at least one of said sections being bifurcated to form a slot,
    a socket formed in said first and second sections for receiving the head of a spinal implant,
    receiving means adapted to receive a support rod, said receiving means being movable relative to said socket to permit adjustment of the distance between a support rod and a surgical implant, and
    compression means for forcing said two sections together to grasp the head of a surgical implant lodged in said socket.

2. The clamp claimed in claim 1 wherein the receiving means comprises a hook having a bight and a shaft extending through the slot, said bight being adapted to receive a support rod.

3. The clamp claimed in claim 2 further comprising a retaining plate on the upper surface of one section, said retaining plate having a hole to receive the shaft of the hook.

4. The clamp claimed in claim 3 further comprising a nut on the end of the shaft of the hook for holding the retaining plate against the upper surface of one section.

5. The clamp claimed in claim 3 wherein the retaining plate and the upper surface of one section have teeth adapted to engage one another.

6. A clamp according to claim 1 wherein the socket is adapted to receive a spherical-headed pedicle screw.

7. A clamp according to claim 1 wherein the socket has roughened surfaces.

8. A clamp according to claim 2 wherein a surface of the bight is threaded for engagement with threads of a support rod.

9. The clamp claimed in claim 1 wherein one of said sections has a roughened surface for contact with a support rod.

10. An assembly comprising:
a clamp according to claim 1,
a support rod; received in said receiving means and
a pedicle screw lodged in said socket.

11. An assembly as claimed in claim 10 wherein the pedicle screw has a spherical head.

12. A clamp according to claim 1 wherein said first section is a front section and said second section is a back section, said front section being bifurcated, and said receiving means comprises:
a hook having a bight below said first section and a threaded shaft extending through the slot in said bifurcated first section, said bight being adapted to receive a support rod,
a retaining plate resting on the upper surface of the bifurcated part of said first section, said retaining plate having a hole to receive the shaft of the hook,
a nut on the end of the shaft of the hook, for holding the retaining plate against the upper surface of the first section,
said retaining plate having serrated a lower surface for engaging a serrated surface on the upper surface of the first section; and wherein
said compression means comprises a screw adapted to fit into a screw hole extending from one section into the other section.

13. A clamp according to claim 12 wherein said screw hole extends from the front section into the back section at an angle of approximately 45° to the axis of the implant.

14. A clamp according to claim 1 wherein:
said first section is a bifurcated upper section,
said second section is a lower section, shorter than said upper section and hingedly connected thereto,
said receiving means comprises:
a hook having a bight below said upper section and a threaded shaft extending through the slot in said bifurcated upper section, said bight being adapted to receive a support rod,
a retaining plate resting on the upper surface of the bifurcated part of said upper section, said retaining plate having a hole to receive the shaft of the hook,
a nut on the end of the shaft of the hook, for holding the retaining plate against the upper surface of the upper section,
said retaining plate having a serrated lower surface for engagement with a serrated surface on the upper section; and
said compression means comprises a screw adapted to fit into a screw hole extending from on section into the other section.

15. A clamp for attaching a spinal implant to a spinal support rod comprising:
a jaw having upper and lower sections hinged at one end, said sections being bifurcated to form a slot extending through said sections,
a socket formed in said jaw for receiving the head of a spinal implant and
compression means for forcing the sections of said jaw together to grasp the head of an implant lodged in said socket, said compression means being adapted to receive a support rod and to urge said rod against said jaw as said jaw sections are forced together, said compression means being movable relative to said socket to permit adjustment of the distance between a support rod and an implant.

16. The clamp claimed in claim 15 wherein the compression means comprises a hook having a bight below said lower jaw section and a threaded shaft extending through the slot in said sections, said bight being adapted to received a support rod. and a threaded shaft extending through the slot in said sections, said bight being adapted to received a support rod.

17. The clamp claimed in claim 16 further comprising a retaining plate resting on the upper surface of the upper section, said retaining plate having a hole to receive the shaft of the hook.

18. The clamp claimed in claim 17 further comprising a nut on the end of the shaft of the hook, which, when tightened, holds the retaining plate against the upper surface of the upper section.

19. The clamp claimed in claim 17 wherein the retaining plate has a lower surface which has teeth that fit into corresponding teeth on the upper surface of the upper section.

20. A clamp according to claim 15 wherein the socket is adapted to receive a spherical-headed pedicle screw.

21. A clamp according to claim 15 wherein the socket has roughened surfaces to grasp the head of an implant.

22. A clamp according to claim 16 wherein a surface of the bight is in contact with a support rod, said surface being threaded.

23. A clamp according to claim 15 wherein the lower section has a lower surface which contacts a support rod.

24. A clamp claimed in claim 23 wherein the contacting surface is roughened.

25. An assembly for treating spinal injuries comprising:
a support rod,
a spinal implant having a head, and
a clamp for attaching the spinal implant to the spinal support rod, said clamp comprising a jaw having upper and lower sections hinged at one end, said sections being bifurcated to form a slot extending through said sections, a socket formed in said jaw for receiving the head of an implant and compression means for forcing the sections of said jaw together to grasp the head of an implant lodged in said socket, said compression means being adapted to receive a support rod and to urge said rod against said jaw as said jaw sections are forced together, said compression means being movable relative to said socket to permit adjustment of the distance between the support rod and the implant.

26. An assembly claimed in claim 25 wherein the implant has a spherical head.

27. A clamp for attaching a spinal implant to a spinal support rod comprising:
- a first section and a second section, at least one of said sections being bifurcated to form a slot,
- a socket formed in aid first and second sections for receiving the head of a spinal implant,
- receiving means adapted to receive a support rod, said receiving means being movable relative to said socket, and comprising a hook having a bight and a shaft extending through the slot, said bight being adapted to receive a support rod, and
- compression means for forcing said two sections together to grasp the head of a spinal implant lodged in said socket.

28. A clamp for attaching a spinal implant to a spinal support rod comprising:
- a front section and a back section, said front section being bifurcated to form a slot,
- a socket formed in said front and back sections for receiving the head of an implant,
- compression means for forcing said two sections together to grasp the head of a surgical implant lodged in said socket, and
- receiving means adapted to receive a support rod, said receiving means being movable relative to said socket, and said receiving means comprising:
  - a hook having a bight below said front section and a threaded shaft extending through the slot in said bifurcated front section, said bight being adapted to receive a support rod,
  - a retaining plate resting on the upper surface of the bifurcated part of said front section, said retaining plate having a hole to receive the shaft of the hook,
  - a nut on the end of the shaft of the hook, for holding the retaining plate against the upper surface of the front section,
  - said retaining plate having a serrated lower surface for engaging a serrated surface on the upper surface of the front section; and wherein
  - said compression means comprises a screw adapted to fit into a screw hole extending from one section into the other section.

29. A clamp for attaching a spinal implant to a spinal support rod comprising:
- a bifurcated upper section,
- a lower section, shorter than said upper section and hingedly connected thereto,
- a socket formed in said upper and lower sections for receiving the head of a spinal implant,
- compression means for forcing said tow sections together to grasp the head of an implant lodged in said socket, said compression means comprising a screw adapted to fit into a screw hole extending from one section into the other section, and
- receiving means adapted to receive a support rod, said receiving means being movable relative to said socket, and said receiving means comprising;
- a hook having a bight below said upper section and a threaded shaft extending through the slot in said bifurcated upper section, said bight being adapted to receive a support rod,
- a retaining plate resting on the upper surface of the bifurcated part of said upper section, said retaining plate having a hole to receive the shaft of the hook, and a serrated lower surface for engagement with a serrated surface on the upper section, and
- a nut on the end of the shaft of the hook, for holding the retaining plate against the upper surface of the upper section.

* * * * *

UNITED STATES PATENT AND TRADEMARK OFFICE
CERTIFICATE OF CORRECTION

PATENT NO. : 5,002,542

DATED : March 26, 1991

INVENTOR(S) : Robert Frigg

It is certified that error appears in the above-identified patent and that said Letters Patent is hereby corrected as shown below:

Claim 14, col. 5, line 67, change "on" to ---one---.

Claim 16, col. 6, lines 21-23, after the "." delete "and a threaded shaft extending through the slot in said sections, said bight being adapted to received a support rod."

Claim 27, col 7, line 5, change "aid" to ---said---.

Claim 29, col. 8, line 24, after "comprising" change the ";" to ---:---.

Signed and Sealed this

Twelfth Day of January, 1993

*Attest:*

DOUGLAS B. COMER

*Attesting Officer*      *Acting Commissioner of Patents and Trademarks*